United States Patent [19]

Hirahara

[11] Patent Number: 5,084,273

[45] Date of Patent: Jan. 28, 1992

[54] COMPOSITION OF ANTICOAGULANTS

[75] Inventor: Keizo Hirahara, Saitama, Japan

[73] Assignee: Hoechst Japan Limited, Tokyo, Japan

[21] Appl. No.: 630,754

[22] Filed: Dec. 21, 1990

Related U.S. Application Data

[63] Continuation of Ser. No. 301,676, Jan. 26, 1989, abandoned.

[30] Foreign Application Priority Data

Jan. 28, 1988 [JP] Japan .................................. 63-15761

[51] Int. Cl.$^5$ ..................... A61K 35/14; A61K 37/04; A61K 37/62
[52] U.S. Cl. .................................. 424/94.6; 530/380; 530/393
[58] Field of Search ................ 530/380, 393; 424/94.6

[56] References Cited

U.S. PATENT DOCUMENTS 4,604,285  8/1986  Smith et al. ........................ 424/94.6

OTHER PUBLICATIONS

McLean, Am. J. of Physiol., vol. 41 (1916) p. 250.
Suzuki et al., J.B.C., vol. 258 (1983) p. 1914.
Miller-Anderson et al., Thrombosis Research (1974), vol. 5, pp. 439-452.

*Primary Examiner*—Howard E. Schain
*Assistant Examiner*—Choon P. Koh
*Attorney, Agent, or Firm*—Finnegan, Henderson, Farabow, Garrett, and Dunner

[57] ABSTRACT

An anticoagulant containing as active ingredients protein C or activated protein C and heparin has a high anticoagulant activity which cannot be obtained with activated protein C or heparin alone. The activity of the anticoagulant is further increased by addition of AT III.

3 Claims, 1 Drawing Sheet

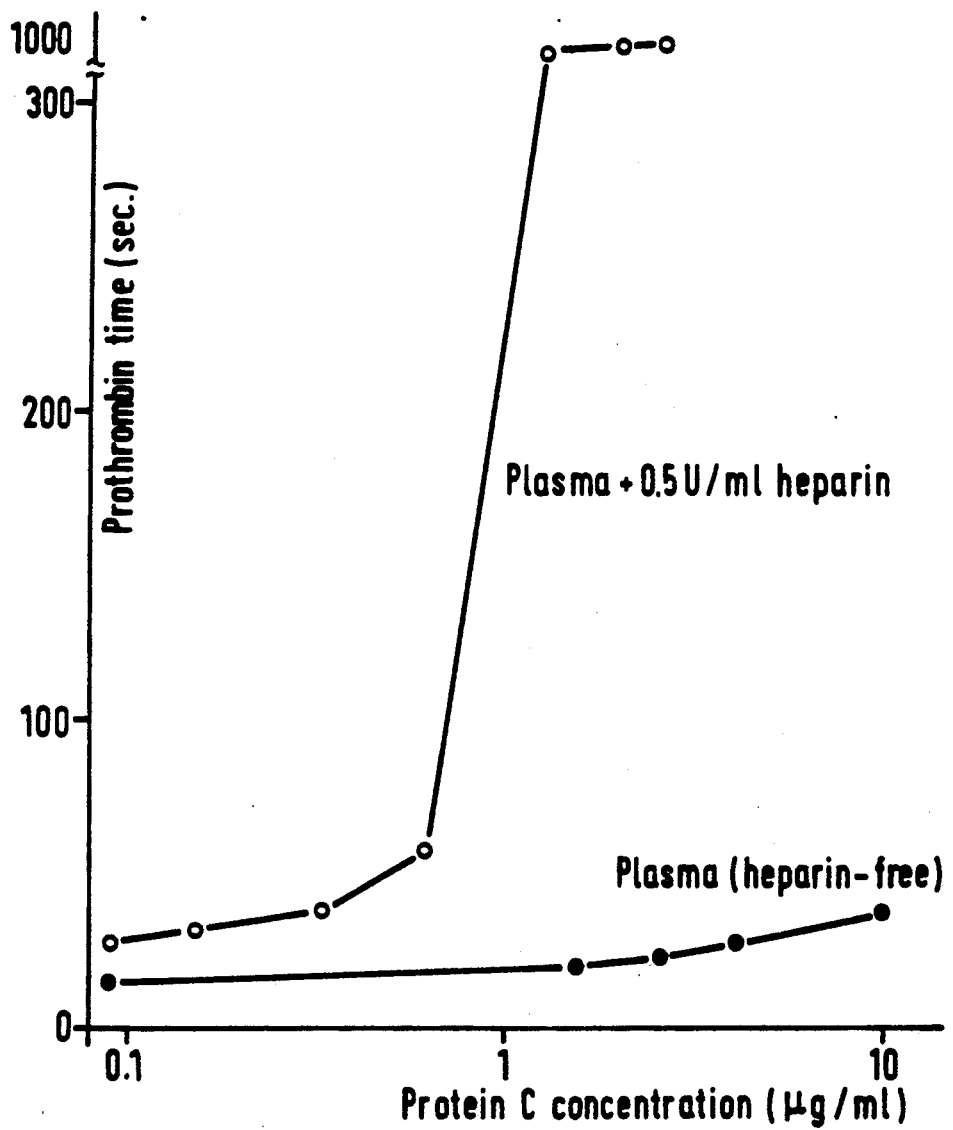

COMPOSITION OF ANTICOAGULANTS

This application is a continuation of application Ser. No. 07/301,676 filed Jan. 26, 1989 now abandoned.

BACKGROUND OF THE INVENTION

1. Field of the invention

The present invention relates to anticoagulants containing as active ingredients protein C or activated protein C and heparin, or protein C or activated protein C, heparin and antithrombin III (called AT III hereinbelow).

2 Prior art

Protein C was isolated and purified by Stenflo from bovine plasma (The Journal of Biological Chemistry, 251(2), 355-363 (1976)) and later by Kisiel from human plasma (The Journal of Clinical Investigation 64, 761-769 (1979)). Presently, it can also be prepared by means of genetic engineering.

It is described in Biochemistry 19, 401-410 (1980), Proc. Natl. Acad. Sci. USA 79, 7200-7204 (1982) and J. Biol. Chem. 258, 1914-1920 (1983) that protein C is activated in vivo by thrombin and thrombomodulin or in vitro by Protac ®, a snake venom, to form activated protein C which inactivates blood coagulation factor VIII and blood coagulation factor V, phospholipid and $Ca^{2+}$.

The role of factor V in the prothrombin activation reactions on phospholipid have been studied since the latter half of 1970s. Conversion rate of prothrombin to thrombin by activated factor X is much accelerated by activated factor V, phospholipid and $Ca^{2+}$. Taking the conversion rate with the prothrombin - activated factor X - $Ca^{2+}$ system as 1, the rate is 22 when phospholipid is added to the composition, 356 when activated factor V is added in place of the phospholipid and 278000 when both the phospholipid and the activated factor V are added. As described above, activated factor V as a protein cofactor plays an important role in activation of precursors of coagulation factors. It is activated protein C that decomposes activated factor V thereby inhibiting its cofactor activity and progress of the coagulation cascade. Activated factor VIII also possesses a protein-cofactor activity and deeply participates in the activation of factor X by activated factor IX. Effect of activated factor VIII on the activation reaction is shown by an increase in the rate of the activation by about 200000 times in the presence of activated factor VIII, $Ca^{2+}$ and phospholipid as compared with the absence of factor VIII and phospholipid. Activated protein C also inactivates factor VIII thereby inhibiting the progress of coagulation cascade.

Heparin was found by Mclean in the liver of dogs as a substance which inhibits blood coagulation (Am. J. Physiol. 41, 250-257, 1916). Seventy years have passed since the discovery of heparin. Now, it is widely used as an anticoagulant which is prepared by separating and purifying it from the liver and intestine of cattle and whale. It is known that the blood coagulation-inhibiting activity of heparin is produced in such that the presence of heparin accelerates the action of AT III in inhibiting thrombin or activafed blood coagulation factor X.

Miller-Anderson et al. published the specific purification method of AT III by so-called affinity chromatography with heparin fixed on agarose (Thromb. Res. 5, 439-452 (1974)). Since then, purification of AT III has become much easier, and AT III is now available world-wide as an anticoagulant in the form of pharmaceutical preparations which are mainly used for the therapy of disseminated intravascular coagulation (DIC). AT III is known to inhibit in vitro activities of thrombin, activated factor IX and activated factor X in blood coagulation. Activated factor X, however, is not inhibited by AT III if it forms a complex with activated factor V, $Ca^{2+}$ and phospholipid. It is believed that the inhibitory effect of AT III in vivo is mainly toward thrombin generated in blood. The effect is much reinforced by heparin.

Blood coagulation includes intrinsic blood coagulation and extrinsic blood coagulation caused via extravascular tissue factors and phospholipid.

Each of these factors does not act independently. As a matter of fact, bleeding occurs at insufficiency of coagulation factor VIII or factor IX which is an intrinsic factor, even if the extrinsic system is normal; bleeding also occurs in factor VII insufficiency even if the intrinsic system is normal. When a small amount of a tissue factor is produced, the tissue factor forms a complex with factor VII, $Ca^{2+}$ and phospholipid, which activates an intrinsic factor, factor IX. This means that without the activation of factor IX by the complex, coagulation will not effectively occur.

The intrinsic system is activated by the contact of factor XII with the connective tissues, particularly with collagen, and through a cascade, activates factor X. On the other hand, the extrinsic system, while activating factor X by the formation of a complex of a tissue factor generated by tissue injury with factor VII, $Ca^{2+}$ and phospholipid, activates intrinsic factor IX to accerelate formation of activated factor X.

Furthermore, the factor X activated by both intrinsic and extrinsic systems forms a complex with factor V which is a cofactor, $Ca^{2+}$ and phospholipid which acts as an activator for prothrombin to result in conversion of prothrombin to thrombin. The thrombin converts fibrinogen to fibrin. In the extrinsic system, the processes from factor XII are bypassed, and therefore, the processes take place within ten and odd seconds. A very small amount of thrombin which has been formed at the early stage acts upon factor V and factor VIII, which in turn are activated thereby further accelerating coagulation. The very small amount of thrombin is known to act also upon platelets and to promote liberation of phospholipid. Thus, it plays a role of the trigger for the intrinsic coagulation in combination with activation by the action of factor XII.

In the coagulation system fibrin is finally formed with many coagulation factors participating in. As previously described, inhibitions during the above processes take place by AT III mainly to thrombin and by protein C to activated factor V and activated factor VIII. AT III is presently used for the therapy of DIC, however the mechanism of its action does not indicate inhibition of the activation process itself, therefore the development of more effective anticoagulants which inhibit not only the activation process but also thrombin activity is desired.

BRIEF DESCRIPTION OF THE DRAWING

FIG. 1 is a graph showing relationship between concentration of protein C and coagulation time.

DETAILED DESCRIPTION OF THE INVENTION

In view of the above-described situation, we made extensive studies on effective anticoagulants. Surprisingly, very high anticoagulant activities not obtained with activated protein C alone or with AT III-heparin have been found according to the present invention. The invention is concerned with anticoagulants containing as the active ingredients human protein C or activated protein C and heparin, or human protein C or activated protein C, heparin and AT III.

The anticoagulants of the invention are administered preferably by injection or infusion. In preparing the injectable pharmaceutical preparation, a pH-adjusting agent, a buffering agent, a stabilizer, an agent for effecting isotonicity and the like may be added to the active ingredients. Lyophilization may further be applied by conventional procedures to prepare freeze-dried injectable preparations. For example, one or more of additives such as mannitol, sucrose, lactose, maltose, glucose, amino acids and albumin may be added to the active ingredients; the mixture is dissolved in water, and the solution is divided into vials or ampules, which are then freeze-dried and tightly sealed to prepare the preparation for intravenous injection.

Protein C as an active ingredient is present in the carrier at a concentration in the range of about 2 µg/ml to 20 µg/ml, AT III in the range of 140-300 µg/ml and heparin in the range of 0.1-1.0 usp unit/ml. The total amount of protein in the active ingredient to be given per dose is in the range of 5 mg to 1 g for an adult weighing 60 kg. Multidoses may occasionally be needed.

Protein C or activated protein C and AT III, which are used as active ingredients in the pharmaceutical preparations of the invention, are human plasma proteins and are of very low toxicity. Heparin is currently put into clinical use and produces no problem of toxicity at all provided that it is properly used.

The invention will be described in more detail with reference to Test Examples and Examples.

TEST EXAMPLE 1

Prolongation of the prothrombin time in protein C-defficient plasma

As protein C was used a product purified by the method of Kisiel (J. Clin. Invest. 64, 761-769, 1979). Activation of the protein C was conducted by the method using Protac ® (Thromb. Res. 43, 253-264, 1986).

Heparin and the activated protein C were added to protein C-defficient plasma. After incubation at 37° C., tissue thromboplastin and CaCl2 solution were added, and coagulation time was measured according to the usual measurement of prothrombin time (Scan. J. Clin. Lab. Invest. 1, 81, 1949). Results are shown in FIG. 1. It is seen from FIG. 1 that although almost no prolongation of the coagulation time was observed in case of activated protein C in the absence of heparin (□—□), a prolongation was observed in the presence of heparin and activated protein C (○—○).

TEST EXAMPLE 2

Prolongation of the prothrombin time by combinations of heparin, AT III and activated protein C in the presence of prothrombin, factor VII, factor X, factor IX and fibrinogen To a mixed solution of prothrombin, factor VII, factor IX and factor X prepared so as to contain each of them at a concentration of one unit/ml was added fibrinogen (4 mg/ml) followed by addition of a solution of heparin, AT III and activated protein C in various combinations. After incubated at 37° C. for 2 min., tissue thromboplastin and CaCl2 solution were added, and coagulation time was measured according to the usual measurement of prothrombin time (Scan. J. Clin. Invest. 1, 81, 1949). Results of the experiments are shown in Table 1. It is seen from Table 1 that coagulation time is much prolonged in the presence of a combination of AT III, heparin and activated protein C.

TABLE 1

| | Prothrombin Time | |
| --- | --- | --- |
| | Coagulation time | |
| Additive | Experiment 1 | Experiment 2 |
| — | 14.8 | 14.7 |
| AT III | 15.1 | 15.2 |
| Heparin | 17.3 | 17.1 |
| APC | 21.4 | 21.2 |
| AT III + heparin | 24.9 | 23.4 |
| APC + heparin | 25.0 | 24.2 |
| APC + AT III | 21.6 | 21.6 |
| APC + AT III + heparin | 76.4 | 102.5 |

APC: Activated protein C

EXAMPLE 1

In order to obtain a 10 ml-preparation, a vial or an ampule was filled with 1.5 mg of protein C or activated protein C, 50 usp units of heparin, 22,5 mg of aminoacetic acid, 25 mg of human serum albumin, 100 mg of D-mannitol, and 90 mg of sodium chloride followed by lyophilization and tight sealing.

EXAMPLE 2

A 10 ml-preparation was prepared by filling a vial or an ampule with 1.5 mg of protein C or activated protein C, 50 mg of AT III, 50 usp units of heparin, 22.5 mg of aminoacetic acid, 25 mg of human serum albumin, 100 mg of D-mannitol and 90 mg of sodium chloride followed by lyophilization and tight sealing.

I claim:

1. An anticoagulant comprising protein C or activated protein C, heparin and antithrombin III, wherein the ratio of protein C or activated protein C, calculated in terms of protein C, heparin, and antithrombin III is 2-20 µg: 0.1-1.0 usp unit: 140-300 µg.

2. A method of treatment for hemostatic disorders, which comprises administering an effective amount as an anticoagulant of a composition containing either protein C or activated protein C and heparin.

3. A method as claimed in claim 2, wherein the composition additionally contains antithrombin III.

* * * * *